United States Patent [19]

Bellani et al.

[11] Patent Number: 4,465,831

[45] Date of Patent: Aug. 14, 1984

[54] KETOIMINOCEPHALOSPORIN DERIVATIVES

[75] Inventors: Piero Bellani, Milan, Italy; Goffredo Bolis, Bergamo; Giampietro Broccali, Milan; Roberto Giani, Milan; Mario Pinza, Milan, all of Italy

[73] Assignee: ISF S.p.A., Milan, Italy

[21] Appl. No.: 332,326

[22] Filed: Dec. 18, 1981

[30] Foreign Application Priority Data

Dec. 24, 1980 [IT] Italy ................................ 26945 A/80

[51] Int. Cl.$^3$ .......................................... C07D 501/28
[52] U.S. Cl. ........................................ 544/26; 544/16; 544/22; 544/27; 544/28; 544/30
[58] Field of Search ...................... 544/27, 30, 16, 22, 544/26, 28

[56] References Cited

FOREIGN PATENT DOCUMENTS 2900961 7/1979 Fed. Rep. of Germany .
2034692 6/1980 United Kingdom .................. 544/22

Primary Examiner—Paul M. Coughlan, Jr.
Attorney, Agent, or Firm—Stevens, Davis, Miller & Mosher

[57] ABSTRACT

There is described a new class of ketohydroxyimino derivatives of cephalosporins of the formula

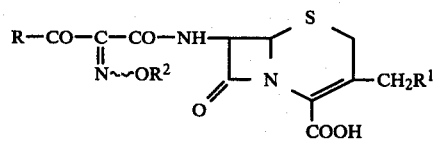

wherein:
R is an alkyl radical having from 2 to 4 carbon atoms, a phenyl, or a 5-membered heterocyclic radical which may be substituted, containing nitrogen, oxygen and/or sulphur;
$R^1$ is an acetoxy, carbamoyloxy or S-heterocyclic group, which may be substituted, and the heterocyclic ring is a 5- or 6-membered ring containing one or more nitrogen atoms, alone or combined with sulphur;
$R^2$ is hydrogen, alkyl or acetyl.

The present compounds have an interesting broad-spectrum antibacterial activity.

6 Claims, No Drawings

KETOIMINOCEPHALOSPORIN DERIVATIVES

The invention relates to ketohydroxyimino derivatives of cephalosporins having antibacterial activity, of the formula

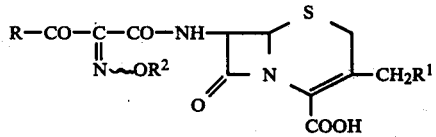

wherein:
R is an alkyl radical having from 2 to 4 carbon atoms, a phenyl or a 5-membered heterocyclic radical which may be substituted, containing nitrogen, oxygen and/or sulphur;
$R^1$ is an acetoxy, carbamoyloxy or S-heterocyclic group, which may be substituted, and the heterocyclic ring is a 5- or 6-membered ring containing one or more nitrogen atoms, alone or combined with sulphur;
$R^2$ is hydrogen, alkyl or acetyl.

The wavy line indicates that compounds of formula I can, depending upon the configuration of such group, have a sin or anti configuration or both.

As particularly preferred heterocyclic groups are furyl, tetrazolyl, thiazolyl, thiophenyl, thiadiazolyl, and piridazynyl, which can be optionally substituted by alkyl and sulphoalkyl radicals containing from 1 to 3 carbon atoms, carboxy or amino groups.

The present invention also comprises pharmaceutically acceptable salts of the compounds of general formula I such as sodium and potassium salts.

The compounds of the present invention can be prepared by reacting under suitable conditions a 7β-aminocephalosporanic derivative

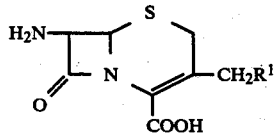

wherein $R^1$ has the same meaning as above, with a suitable compound

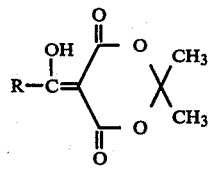

wherein R has the same meaning as above and treating the product thus formed

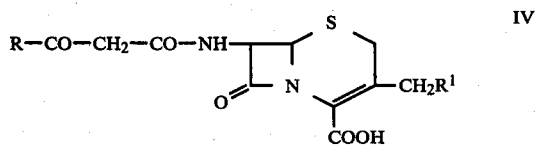

wherein R and $R^1$ have the same meaning as above, with an alkali nitrite in the presence of a suitable acid to give the compounds of formula I in which $R^2$ is hydrogen. The reaction between compounds II and III occurs in an aprotic solvent having a low boiling point and preferably it is carried out at a temperature of from 25° to 100° C. Among the solvents, tetrahydrofuran, methylene chloride and chloroform are particularly suitable.

The carboxylic group of cephalosporanic derivatives II generally protected by a suitable group such as N,O-bistrimethylsilylacetamide. As an alternative to sodium or potassium nitrites, organic nitrites such as amyl, methyl or isoamyl nitrite can be used for the nitrosation reaction. The reaction between compound IV and the alkali nitrite is carried out in the presence of a suitable acid. The preferred acids are acetic or formic acids.

Compounds of formula I, in which $R^2$ is alkyl or acetyl can be prepared by known alkylation and acylation techniques from corresponding compounds in which $R^2$ is hydrogen while the free carboxylic groups are protected, or they can be obtained directly by condensing 3-oxo-2-alkoxy-(or -acyloxy) iminoalkanoic acid with a 7β-aminocephalosporanic derivative II. Alternatively, compounds I in which $R^2$ is hydrogen can be prepared by reacting compound III with 7β-aminocephalosporanic acid and then replacing the acetoxymethyl group in the 3-position with the desired group as the last reaction step after nitrosation and acylation or alkylation.

Compounds of the invention have antibacterial activity against gram-negative microorganisms, including some β-lactamase producing microorganisms. They also have valuable activity against gram-positive microorganisms.

The antibacterial activity "in vitro" has been evaluated to determine the minimum inhibiting concentration (MIC) for gram-positive and gram-negative microorganisms including some β-lactamase producers in agriculture soil (isosensitest agar OXOID). As bacterial inoculum, a culture grown overnight at 37° C. and diluted in a liquid culture soil (1/25) at the time of the use was employed.

The compounds of the invention have been evaluated using as the standard the known compound "cefuroxime" in comparison with which they displayed considerably more activity on gram-positive and gram-negative microorganisms. The experimental results listed in the Table are expressed in γ/ml and represent the average value of four experiments carried out under the same experimental conditions.

TABLE

| MICROORGANISMS | CEFUR-OXIME | 7β-(2-hydroxyimino-3-oxo-valeramido)-3-acetoxy-methylceph-3-em-carbo-xylic acid (C76) | 7β-(2-hydroxyimino-3-oxo-4-methylvaleramido) 3-acetoxymethylceph-3-em-4-carboxylic acid (C84) | 7β-(2-hydroxyimino-3-oxo-valeramido) 3-[(1-methyl-1H—tetrazol-5-yl)thiomethyl] ceph-3-em-4-carboxylic acid (C89) |
|---|---|---|---|---|
| Gram + | | | | |
| S. aureus ATCC 9144 | 0.62 | 0.39 | 0.19 | 0.13 |
| S. aureus 6014668 | 56.2 | 9.3 | 12.5 | 9.04 |

TABLE-continued

| MICROORGANISMS | CEFUR-OXIME | 7β-(2-hydroxyimino-3-oxo-valeramido)-3-acetoxy-methylceph-3-em-carbo-xylic acid (C76) | 7β-(2-hydroxyimino-3-oxo-4-methylvaleramido) 3-ace-toxymethylceph-3-em-4-carboxylic acid (C84) | 7β-(2-hydroxyimino-3-oxo-valeramido) 3-[(1-methyl-1H—tetrazol-5-yl)thiomethyl] ceph-3-em-4-carboxylic acid (C89) |
|---|---|---|---|---|
| (penicillinase producer) S. aureus F2 | 24.3 | 6.25 | 6.25 | 9.04 |
| (penicillinase producer) S. faecalis ATCC 6057 | 45 | 18.7 | 25 | 12.5 |
| S. lutea ATCC 9341 | 0.056 | 0.012 | 0.012 | 0.012 |
| E. coli R+ TEM (β-lactamase producer) | 4.4 | 3.12 | 6.25 | 0.55 |
| S. typhi 6/12 To | 1.56 | 0.39 | 1.56 | 0.067 |
| S. typhimurium | 6.25 | 3.12 | 6.25 | 0.55 |
| E. cloacae 214 (β-lactamase producer) | 17.6 | 9.31 | 12.5 | 1.56 |
| S. paratyphi B | 8.83 | 3.12 | 6.25 | 0.27 |
| E. cloacae E 53 (β-lactamase producer) | 17.6 | 9.31 | 12.5 | 2.2 |

EXAMPLE 1

7β-(2-hydroxyimino-3-oxovaleramido)-3-acetoxymethylceph-3-em-4-carboxylic acid

A suspension of 8.2 g. 7β-aminocephalosporanic acid in 100 ml. of tetrahydrofuran and 24 ml. of N,O-bis-trimethylsilylacetamide is heated to reflux and stirred for two hours to yield a limpid solution. 6 grams of 2,2-dimethyl-4,6-dioxo-5-propanoyl-1,3-dioxane are added and the mixture is stirred for 3 hours at reflux and then cooled to room temperature and evaporated to dryness. The residue is dissolved in 300 ml. of ethyl acetate and 200 ml. of water. The insoluble phase is filtered off and separated. The organic phase is washed with 100 ml. of water, dried, decolourised over charcoal and evaporated to dryness. The residue is taken up with diisopropyl ether and a gummy product is obtained, which is triturated with diethyl ether to give 2 g. of 7β-(2-oxovaleramido)-3-acetoxymethylceph-3-em-4carboxylic acid melting at 127°–134° C. (with decomposition). To a solution of 1.6 g. of 7β-(3-oxovaleramido)-3-acetoxymethylceph-3-em-4-carboxylic acid in 25 ml of glacial acetic acid are added dropwise 0.6 g of sodium nitrite dissolved in 6 ml. of water. The mixture is stirred for one hour and a half, then 100 ml. of ethyl acetate and 100 ml. of a saturated solution of sodium chloride are added thereto. The organic phase is separated, washed twice with 50 ml. of water, made anhydrous and concentrated to small volume. The precipitate is filtered off and gives 0.9 g. of 7β-(2-hydroxyimido-3-oxovaleramido)-3-acetoxymethylceph-3-em-4-carboxylic acid melting at 190°–204° C. (with decomposition); [α]$_D$= +97° C. (c=0.2 in tetrahydrofuran/water 1:1).

EXAMPLE 2

7β-(2-hydroxyimino-3-oxo-4-methylvaleramido)-3-acetoxymethylceph-3-em-4-carboxylic acid To a solution of 14.4 g. of 2,2-dimethyl-1,3-dioxane-4,6-dione in 150 ml. of methylene chloride are added 19.4 ml. of pyridine. After cooling to 0° C., 140 ml. of 9% isobutyryl chloride in chloroform are slowly added thereto; then the reaction mixture is stirred for 1 hour at 0° C. and then for a further hour at ambient temperature. It is evaporated to dryness, the residue is taken up with 500 ml. of ethyl acetate and stirred for 30 minutes, then filtered and the collected solid is discarded. The limpid filtrate is extracted twice with a 6.9% sodium bicarbonate solution in water and the aqueous extracts are collected and covered with 500 ml. of ethyl acetate and acidified to pH 1.5 with 20% hydrochloric acid. The phases are separated and the aqueous phase is re-extracted with 100 ml. of ethyl acetate. The collected organic extracts are washed with 100 ml. of saturated sodium chloride solution, then dried over magnesium sulphate, decolourised over charcoal and evaporated to dryness, to give 12 g. of 2,2-dimethyl-5-isobutyryl-1,3-dioxane-4,6-dione in oily form. I.R./film=1745, 1667, 1580 cm$^{-1}$. A suspension of 12.7 g. of 7β-aminocephalosporanic acid in 120 ml. tetrahydrofuran and 37.5 ml. of N,O-bistrimethylsilylacetamide is stirred for 1 hour at ambient temperature to yield a limpid solution. To the mixture are added 12.2 g. of 2,2-dimethyl-4,6-dione-5-isobutyryl-1,3-dioxane and it is heated to 60° C. for one hour and a half. It is cooled at ambient temperature, evaporated to dryness and the residue is dissolved in 300 ml. of ethyl acetate and 200 ml of water.

The insoluble residue is removed by filtration and the phases are separated. The organic phase is washed with 50 ml of water, made anhydrous, decolourised over charcoal and concentrated to small volume.

A solution 1M 2-ethyl sodium hexanoate in methylisobutylketone is added thereto until pH 8, then it undergoes stirring for 20 hours, then the precipitate is filtered off to give 10.8 g of sodium salt of 7β-(3-oxo-4-methylvaleramido)-3-acetoxymethylceph-3-em-4-carboxylic acid melting at 183°–185° C. (with decomposition).

To a solution of 6.1 g. of sodium salt of 7β-(3-oxo-4-methylvaleramido)-3-acetoxymethylceph-3-em-4-carboxylic acid in 60 ml. of glacial acetic acid, are dropped 2.1 g. of sodium nitrite dissolved in 20 ml. of water. After stirring for 2 hours at ambient temperature, there are added 200 ml. of ethyl acetate and 100 ml. of hydrochloric acid 0.1N. The phases are separated and the organic phase is washed with 50 ml. of water, made anhydrous, decolourised over charcoal and concentrated to small volume. The precipitated solid is filtered off to give 1.4 g of 7β-(2-hydroxyimino-3-oxo-4-methylvaleramido)-3-acetoxymethylceph-3-em-4-carboxylic acid melting at 156° C. (with decomposition); [α]$_D$= +76.9° C. (c=2 in tetrahydrofuran/water 1:1).

EXAMPLE 3

7β-[(2-hydroxyimino-3-oxo-3-phenyl)propionamido]-3-acetoxymethylceph-3-em-4-carboxylic acid 14.4 grams of 2,2-dimethyl-1,3-dioxane-4,6-dione in 200 ml. of anhydrous tetrahydrofuran and 11 g. of 50% sodium hydride in mineral oil are stirred for one hour and then treated dropwise with a solution of 15 ml. of benzoyl chloride in 50 ml. anhydrous tetrahydrofuran. After stirring for 16 hours, the product is evaporated in vacuo to dryness; the residue is taken up with 200 ml. of diethyl ether, filtered, dissolved in 100 ml. of water and filtered off. The aqueous solution is acidified with 10% hydrochloric acid and extracted with 100 ml. of ethyl acetate. The organic phase is made anhydrous over magnesium sulphate and evaporated in vacuo to dryness. The residue is slurried in diethyl ether and filtered to give 11.8 g. of 2,2-dimethyl-5-benzoyl-1,3-dioxane-4,6-dione which melts at 107°–108° C. (with decomposition).

5 grams of 7-aminocephalosporanic acid, 15 ml. of bistrimethylsilyl-acetamide and 100 ml. of tetrahydrofuran are stirred at ambient temperature for 45 minutes, and to the mixture are added 5 g. of 2,2-dimethyl-5-benzoyl-1,3-dioxane-4,6-dione. The product is concentrated to dryness in vacuo after an hour and twenty minutes. The residue is taken up with 100 ml. of ethyl acetate and the resulting solution is stirred with 20 ml. of water for 15 minutes. The organic phase is separated, made anhydrous over magnesium sulphate and evaporated in vacuo to small volume. A white crystalline solid is removed by filtration to give 6.35 g. of 7β-(3-phenyl-3-oxo-propionamide)-3-acetoxymethylceph-3-em-4-carboxylic acid melting at 173°–174° C. (with decomposition) $[α]_D = +63.9°$ C. (c=1 in tetrahydrofuran).

To a solution of 4.8 g. of 7β-(3-phenyl-3-oxopropionamide)-3-acetoxy-methylceph-3-em-4-carboxylic acid in 115 ml. of acetic acid is added dropwise over 10 minutes a solution of 1.58 g. sodium nitrite in 11.5 ml. of water. After stirring for 1 hour, the mixture is poured into 500 ml. of ethyl acetate. The so-obtained solution is washed four times with 100 ml. of water, made anhydrous over magnesium sulphate and evaporated to dryness in vacuo. The residue is slurried in isopropyl ether and filtered to give 5.1 g. of 7β-[(2-hydroxyimino-3-oxo-3-phenyl)propionamide]-3-acetoxymethylceph-3-em-4-carboxylic acid melting at 115°–135° C. (with decomposition); $[α]_D = +41.30°$ (c=1 in tetrahydrofuran).

EXAMPLE 4

7β-[3-(2-furyl)-2-hydroxyimino-3-oxopropionamide]-3-acetoxymethylceph-3-em-4-carboxylic acid Operating in a way similar to that above described using 2,2-dimethyl-4,6-dioxo-5-(2-furoyl)-1,3-dioxane (obtained using furoyl chloride instead of isobutyryl chloride) is obtained at first 7β-[3-(2-furyl)-3-oxopropionamido]-3-acetoxymethylceph-3-em-4-carboxylic acid (melting point 170°–171° C.), and then 7β-[3-(2-furyl)-2-hydroxyimino-3-oxopropionamido]-3-acetoxymethylceph-3-em-4-carboxylic acid melting over 300° C. (with decomposition); $[α]_D = +43.5$ (c=1 in acetone).

EXAMPLE 5

7β-(2-hydroxyimino-3-oxovaleramido)-3-[(1-methyl-1H-tetrazol-5-yl)-thiomethyl]ceph-3-em-4-carboxylic acid A suspension of 3.3 g. of 7β-amino-3-[(1-methyl-1H-tetrazol-5-yl)thiomethyl]-ceph-3-em-4-carboxylic acid in 50 ml. of tetrahydrofuran and 8 ml. of N,O-bistrimethylsilylacetamide is stirred for 30 minutes. 2 g. of 2,2-dimethyl-4,6-dioxo-5-propanoyl-1,3-dioxane are added thereto, then the mixture is stirred for 24 hours, evaporated to dryness, and the residue is taken up with 200 ml. of ethyl acetate and 150 ml. of 5% hydrochloric acid. After stirring for 15 minutes, the insoluble matter is removed by filtration, the organic phase is separated and washed with 50 ml. of water, made anhydrous, decolourised over charcoal and concentrated to small volume. To it are added 50 ml. of isopropyl alcohol and a solution 1M 2-ethylhexanoate sodium in isopropyl alcohol to yield a slightly alkaline reaction. The mixture is allowed to stand for 20 hours, then the precipitate is filtered off to give 1.7 g. of sodium salt of 7β-(3-oxovaleramido)-3-[(1-methyl-1H-tetrazol-5-yl)-thiomethyl]-ceph-3-em-4-carboxylic acid, melting at 144°–145.5.° C. (with decomposition).

To a solution of 1.7 g. of sodium salt of 7β-(3-oxovaleramido)-3-[(1-methyl-1H-tetrazol-5-yl)-thiomethyl]-ceph-3-em-4-carboxylic acid in 20 ml. of glacial acetic acid are added 0.5 g. of sodium nitrite dissolved in 5 ml. of water. After stirring for one hour and a half at ambient temperature, 100 ml. of ethyl acetate and 50 ml. of 5% hydrochloric acid are added to the mixture. The phases are separated and the organic phase is washed with 50 ml. of water, made anhydrous, decolourised over charcoal and evaporated to dryness. The residue is triturated with diethyl ether to give 0.7 g. of 7β-(2-hydroxyimino-3-oxovaleramido)-3-[(1-methyl-1H-tetrazol-5-yl)-thiomethyl]ceph-3-em-4-carboxylic acid, melting at 79°–87° C. (with decomposition); $[α]_D = -25°$ C. (c=0.2 in tetrahydrofuran/water 1:1).

EXAMPLE 6

7β-(2-hydroxyimino-3-oxovaleramido)-3-[(1-sulphomethyltetrazol-5-yl)-thiomethyl]ceph-3-em-4-carboxylic acid A mixture of 0.82 g. of 7β-(2-hydroxyimino-3-oxovaleramido)-3-acetoxy-methylceph-3-em-4-carboxylic acid, 0.34 g. of sodium bicarbonate and 0.4 g. of disodium salt of 1-sulphomethyltetrazol-5-thiol in 30 ml. of phosphate buffer at pH 6.5 is heated for 4 hours at 60° C. It is then cooled to 0° C. and acidified to pH 1 with 10% hydrochloric acid. It is filtered, and the filtrate is washed with ethyl acetate and evaporated to dryness in vacuo. The residue is taken up with methyl alcohol, the insoluble portion is removed by filtration and the filtrate is evaporated to dryness. The residue from ethyl alcohol and acetonitrile is triturated to give 0.2 g. of 7β-(2-hydroxyimino-3-oxovaleramido)-3-[(1-sulphomethyltetrazol-5-yl)-thiomethyl]ceph-3-em-4-carboxylic acid, melting over 145° C. (with decomposition); $[α]_D = +8.7°$ (c=0.5% in buffer phosphate pH 7.4).

EXAMPLE 7

7β-(2-hydroxyimino-3-oxovaleramido)-3-[(3-carboxypyridazin-6-yl)thiomethyl]ceph-3-em-4-carboxylic acid Operating as above described and using 0.26 g. of 6-mercaptopyridazin-3-carboxylic acid, 0.11 g. of 7β-(2-hydroxyimino-3-oxovaleramido)-3-[(3-carboxypyridazin-6-yl)-thiomethyl]ceph-3-em-4-carboxylic acid are obtained, melting over 170° C. (with decomposition); $[\alpha]_D = +18.8°$ (c=1% in buffer phosphate pH 7.0).

EXAMPLE 8

7β-(2-hydroxyimino-3-oxovaleramido)-3-carbamoyloxymethylceph-3-em-4-carboxylic acid To a suspension of 2.7 g. of 7β-amino-3-carbamoyloxymethylceph-3-em-4-carboxylic acid in 40 ml. of tetrahydrofuran are added 8 ml. of N,O-bistrimethylsilylacetamide. The mixture is heated to reflux for 2 hours and to the so-obtained limpid solution are added 2 g. of 2,2-dimethyl-4,6-dioxo-5-propionyl-1,3-dioxane. The product is then stirred at reflux for 2 hours, and evaporated to dryness. The residue is dissolved in 150 ml. of ethyl acetate and to the resulting solution are added 50 ml. of 5% hydrochloric acid, and this solution is then stirred for another 15 minutes. The impurities are removed by filtration and the organic phase is separated and washed with 50 ml. of water, made anhydrous over magnesium sulphate, decolourised over charcoal and evaporated to dryness. The residue is triturated with diethyl ether and re-crystallized from ethyl acetate to give 0.65 g. of 7β-(3-oxovaleramido)-3-carbamoyloxymethylceph-3-em-4-carboxylic acid, melting at 152° C. (with decomposition).

To a solution of 1 g. of 7β-(3-oxovaleramido)-3-carbamoyloxymethylceph-3-em-4-carboxylic acid in 25 ml. of 70% acetic acid is added over 30 minutes a solution of 0.37 g. of sodium nitrite in 5 ml. of water. After stirring at ambient temperature for 2 hours, 100 ml. of ethyl acetate are added thereto. The solution is washed with 50 ml. of a saturated sodium chloride solution, then with 50 ml. of water. The organic phase is dried over magnesium sulphate, decolourised over charcoal and evaporated to dryness. By trituration of the residue with diethyl ether are obtained 0.45 g. of 7β-(2-hydroxyimino-3-oxovaleramido)-3-carbamoyloxymethylceph-3-em-4-carboxylic acid melting at 151°-157° C. (with decomposition).

EXAMPLE 9

7β-(2-hydroxyimino-3-oxovaleramido)-3-[(5-methyl-1,3,4-thiadiazol-2-yl)-thiomethyl]ceph-3-em-4-carboxylic acid To a suspension of 3.4 g. of 7β-amino-3-[(5-methyl-1,3,4-thiadiazol-2-yl)thiomethyl]ceph-3-em-4-carboxylic acid in 50 ml. of tetrahydrofuran are added 8 ml. of N,O-bistrimethylsilylacetamide. It is refluxed for 2 hours and to the limpid solution obtained are added 2 g. of 2,2-dimethyl-4,6-dioxo-5-propionyl-1,3-dioxane. The mixture is stirred to reflux for 2 hours, then evaporated to dryness in vacuo. The residue is dissolved in 150 ml. of ethyl acetate, and to the resulting solution are added 50 ml. of 5% hydrochloric acid. After stirring for 15 minutes, the impurities are removed by filtration and the organic phase is separated, washed with 50 ml. of water, made anhydrous over magnesium sulphate, decolourised over charcoal and concentrated to small volume. A crystalline solid is obtained which is filtered and evaporated to give 1.5 g. of 7β-(3-oxovaleramido)-3-[(5-methyl-1,3,4-thiadiazol-2-yl)thiomethyl]ceph-3-em-4-carboxylic acid melting at 146°-149° C. (with decomposition).

To a solution of 1.1 g. of 7β-(3-oxovaleramido)-3-[(5-methyl-1,3,4-thiadiazol-2-yl)thiomethyl]ceph-3-em-4-carboxylic acid in 25 ml. of 60% acetic acid is added in 30 minutes a solution of 0.35 g. of sodium nitrite in 50 ml. of water. After stirring at ambient temperature for 2 hours, 100 ml. of ethyl acetate are added thereto and the solution is washed with 50 ml. of a saturated sodium chloride solution and with water. The organic phase is made anhydrous over magnesium sulphate, decolourised over charcoal and evaporated to dryness. Trituration of the residue with diethyl ether gives 0.5 g. of 7β-(2-hydroxyimino-3-oxovaleramido)-3-[(5-methyl-1,3,4-thiadiazol-2-yl)thiomethyl]ceph-3-em-4-carboxylic acid melting at 118°-119° C. (with decomposition).

EXAMPLE 10

7β-(2-acetoxyimino-3-oxovaleramido)-3-acetoxymethylceph-3-em-4-carboxylic acid

To a solution of 3 g. of 7β-(2-hydroxyimino-3-oxovaleramido)-3-acetoxy-methylceph-3-em-4-carboxylic acid in 50 ml. of tetrahydrofuran are added 1.42 ml. of acetic anhydride. After stirring at ambient temperature for 3 hours, the mixture is evaporated to dryness, and the residue is recrystallized from methylene chloride to give 2.1 g. of 7β-(2-acetoxyimino-3-oxovaleramido)-3-acetoxymethylceph-3-em-4-carboxylic acid, melting at 161° C. (with decomposition).

EXAMPLE 11

7β-(2-methoxyimino-3-oxovaleramido)-3-acetoxymethylceph-3-em-4-carboxylic acid

To a solution of 5 g. of 7β-(3-oxovaleramido)-3-acetoxymethylceph-3-em-4-carboxylic acid in 100 ml. of tetrahydrofuran are added dropwise 3.18 g. of diphenyldiazomethane dissolved in 50 ml. of tetrahydrofuran and the mixture is stirred at ambient temperature for 5 hours. After evaporation to dryness in vacuo, it is triturated with hexane. Then the solid, which separates by filtration, is triturated with diethyl ether, to give 4.4 g. of benzhydryl ester of 7β-(3-oxo-valeramido)-3-acetoxymethylceph-3-em-4-carboxylic acid melting at 105.8°-107.1° C.

To a solution of 6 g. of benzhydryl ester of 7β-(3-oxovaleramido)-3-acetoxymethylceph-3-em-4-carboxylic acid in 20 ml. of glacial acetic acid are added dropwise 1.54 g. of sodium nitrite dissolved in 15 ml. of water, and the mixture is stirred for 2 hours at ambient temperature. The mixture is then diluted with 500 ml. of ethyl acetate and washed 3 times with 100 ml. of an aqueous saturated sodium chloride solution. The organic phase is made anhydrous and evaporated to dryness and the residue is triturated with diethyl ether. 5.5 g. of benzhydryl ester of 7β-(2-hydroxyimino-3-oxovaleramido)-3-acetoxymethylceph-3-em-4-carboxylic acid melting at 56°-62° C. are obtained.

To a solution of 16 g. of benzhydryl ester of 7β-(2-hydroxyimino-3-oxo-valeramido)-3-acetoxymethylceph-3-em-4-carboxylic acid in 175 ml. of tetrahydrofuran is added a solution of 1.75 g. of diazomethane in 100 ml. of diethyl ether. The mixture is stirred at ambient temperature for 30 minutes and evaporated to dryness. The residue is triturated with diethyl ether and chromatographed (silica gel, hexane/ethyl acetate 6:4) to give 3 g. of benzhydryl ester of 7β-(2-methoxyimino-3-oxovaleramido)-3-acetoxymethylceph-3-em-4-carboxylic acid, melting at 164°–168° C.

To a solution of 2 g. of benzhydryl ester of 7β-(2-methoxyimino-3-oxovaleramido)-3-acetoxymethylceph-3-em-4-carboxylic acid in 10 ml. of anisole cooled to 0° C. are added dropwise 8 ml. of trifluoroacetic acid. The reaction mixture is stirred at 0° C. for 30 minutes, then 200 ml. of diethyl ether are added and the mixture is stirred for 1 hour at room temperature. The solid is collected in vacuo to give 0.9 g. of 7β-(2-methoxyimino-3-oxovaleramido)-3-acetoxymethylceph-3-em-4-carboxylic acid, melting at 175.7°–181° C.

EXAMPLE 12

7β-(2-methoxyimino-3-oxovaleramido)-3-[(1-methyl-1H-tetrazol-5-yl)thiomethyl]ceph-3-em-4-carboxylic acid To a solution of 7.5 g. of 7β-(2-hydroxyimino-3-oxovaleramido)-3-[1-methyl-1H-tetrazol-5-yl)thiomethyl]ceph-3-em-4-carboxylic acid in 100 ml. of acetone and 100 ml. of water, cooled to 0° C., are added portionwise 5 g. of sodium carbonate and then dropwise 7.4 ml. of dimethylsulphate. This is stirred for 30 minutes and then 5 g of sodium carbonate and 3.7 ml. of dimethylsulphate are added. Stirring is maintained for one hour, 350 ml. of water are added, the pH is adjusted to 2 with 10% hydrochloric acid and the aqueous layer is extracted with ethyl acetate. The extract is washed with water, made anhydrous and evaporated to dryness. The oily residue thus obtained is washed with hexane several times, is triturated with 100 ml. of diethyl ether, separated in vacuo and extracted with 125 ml. of ethyl acetate. The insoluble phase is removed and the limpid filtrate evaporated to dryness in vacuo is triturated with diethyl ether to give by vacuum separation 1.7 g. of 7β-(2-methoxyimino-3-oxovaleramido)-3-[(1-methyl-1H-tetrazol-5-yl)thiomethyl]ceph-3-em-4-carboxylic acid, melting over 67° C. (with decomposition). [α]$_D$= −38.3° (c=0.2 in tetrahydrofuran/water 1:1).

EXAMPLE 13

7β-[2-hydroxyimino-3-(2-aminothiazol-4-yl)-3-oxopropionamido]-3-acetoxymethylceph-3-em-4-carboxylic acid A solution obtained from 21.4 g. of 2-t-butoxycarbonylaminothiazol-4-yl carboxylic acid, 13.1 ml. of triethylamine and 500 ml. of anhydrous tetrahydrofuran is cooled to 0° C., and 9.17 ml of ethyl chloroformate are added to it. After stirring for 30 minutes at 0° C., the triethylamine hydrochloride is filtered off in vacuo and the resulting solution is added to a solution obtained from 12.7 g. of 2,2-dimethyl-1,3-dioxane-4,6-dione, 9.6 g. of 50% sodium hydride in oil and 400 ml. of anhydrous tetrahydrofuran reacted for one hour at room temperature. The reaction mixture is stirred at room temperature for a further 20 hours, then the solvent is removed by evaporation in vacuo. The residue is taken up with 400 ml. of ethyl acetate and 100 ml. of 1N hydrochloric acid, the organic layer is separated and made anhydrous on magnesium sulphate, the solvent is removed by evaporation in vacuo, and the residue is triturated with isopropyl ether and filtered in vacuo to give 18 g. of 2,2-dimethyl-5-[1-hydroxy-1-(2-t-butoxycarbonylaminothiazol-4-yl)methylene]-1,3-dioxane-4,6-dione melting at 240°–250° C. (with decomposition).

To a suspension of 2.3 g. of 2,2-dimethyl-5-[1-hydroxy-1-(2-t-butoxycarbonylaminothiazol-4-yl)methylene]1,3-dioxane-4,6-dione in 30 ml. of anhydrous dioxane is added a solution obtained by refluxing for 5 minutes 1.53 g. of 7-aminocephalosporanic acid, 4.61 ml. of N,O-bistrimethylsilylacetamide and 75 ml. of anhydrous dioxane. This is boiled for 15 minutes, the solvent is removed for evaporation in vacuo, and the residue is taken up with 50 ml. of ethyl acetate and 30 ml. of 1N hydrochloric acid. The mixture is stirred for 10 minutes, the phases are separated and the organic phase is washed with 10 ml. of a sodium chloride saturated solution and is then made anhydrous over magnesium sulphate. The solvent is removed in vacuo, the residue taken up with diethyl ether and filtered in vacuo to give 1.25 g. of 7β-[3-(2-t-butoxycarbamoylaminothiazol-4-yl)-3-oxopropionamido]-3-acetoxymethylceph-3-em-4-carboxylic acid. TLC [silicagel F 254 # eluant: 1,2-dichloroethane-7-methanol 3]; RF 0.31. To a solution of 7β[3-(2-t-butoxycarbonylaminothiazol-4-yl)-3-oxopropionamido]-3-acetoxymethylceph-3-em-4-carboxylic acid in 24 ml. of glacial acetic acid are added 0.30 g. of sodium nitrite dissolved in 24 ml. of water. The mixture is stirred for 30 minutes at ambient temperature. The solvent is removed by evaporation in vacuo, the residue is taken up with 120 ml. of ethyl acetate and 60 ml. of 0.1N hydrochloric acid. The layers are separated and the organic layer is made anhydrous on magnesium sulphate and evaporated in vacuo to dryness. The residue is triturated with isopropyl ether and filtered, giving 1.20 g. of 7β-[2-hydroxyimino-3-(2-t-butoxycarbonylaminothiazol-4-yl)-3-oxopropionamido]-3-acetoxymethylceph-3-em-4-carboxylic acid. TLC [silicagel F 254 # eluent: chloroform 7-methanol 3]; RF 0.30 and 0.27.

A solution of 0.30 g. of 7β-[2-hydroxyimino-3-(2-t-butoxycarbonylaminothiazol-4-yl)-3-oxopropionamido]-3-acetoxymethylceph-3-em-4-carboxylic acid, 3.2 ml. of anisole and 6.4 ml. of trifluoroacetic acid are stirred for 75 minutes at room temperature, then evaporated in vacuo, and taken up with 50 ml. of diethyl ether and 50 ml. of a 3% sodium bicarbonate. The layers are separated, and to the aqueous layer are added 50 ml. of tetrahydrofuran, hydrochloric acid to pH 3, and then sodium chloride to saturation. The layers are separated and the organic layer is washed with a saturated sodium solution, made anhydrous over magnesium sulphate and evaporated to dryness in vacuo. The residue is taken up with acetone, the solid filtered off, and the solution evaporated to dryness in vacuo. The residue thus obtained is triturated with diethyl ether and filtered to give 0.50 g. of 7β-[2-hydroxyimino-3-(2-aminothiazol-4-yl)-3-oxopropionamido]-3-acetoxymethylceph-3-em-4-carboxylic acid melting over 140° C. (with decomposition). TLC [silicagel F 254 # eluent: ethylacetate 6-acetic acid 2] RF 0.70 and 0.57.

We claim:

1. Ketoiminocephalosporins of the formula

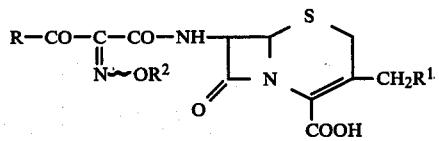

wherein:

R is an alkyl radical having from 2 to 4 carbon atoms, a phenyl or a 5-membered heterocyclic radical selected from the group consisting of furyl, thiazolyl and aminothiazolyl;

$R^1$ is an acetoxy, carbamoyloxy or a S-5- or 6-membered heterocyclic ring containing one or more nitrogen atoms, alone or combined with sulphur, and unsubstituted or substituted with an alkyl or sulphoalkyl radical containing one to three carbon atoms or with a carboxy or an amino group;

$R^2$ is hydrogen, alkyl having one or two carbon atoms or acetyl, provided that $R^2$ is hydrogen when R is an alkyl radical.

2. Pharmaceutically acceptable alkali metal salts of the ketohydroxyiminocephalosporins of claim 1.

3. Ketoiminocephalosporins of the formula

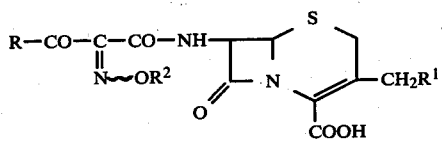

wherein:

R is an alkyl radical having from 2 to 4 carbon atoms, phenyl, furyl, thiophenyl, or thiazolyl;

$R^1$ is acetoxy, carbamoyloxy or an S-heterocyclic group, in which the heterocyclic ring is selected from among tetrazolyl, thiadiazolyl, and pyridazinyl groups, substituted with alkyl and sulphoalkyl groups having from 1 to 3 carbons or carboxy groups;

$R^2$ is hydrogen, alkyl having 1 or 2 carbon atoms, or acetyl, provided that $R^2$ is hydrogen when R is an alkyl radical.

4. The ketohydroxyiminocephalosporin according to claim 1 which is 7β-(2-hydroxyimino-3-oxovaleramido)-3-acetoxymethylceph-3-em-4-carboxylic acid.

5. The ketohydroxyiminocephalosporin according to claim 1 which is 7β-(2-hydroxyimino-3-oxo-4-methylvaleramido)-3-acetoxymethylceph-3-em-4-carboxylic acid.

6. The ketohydroxyiminocephalosporin according to claim 1 which is 7β-(2-hydroxyimino-3-oxovaleramido)-3-[(1-methyl-1H-tetrazol-5-yl)-thiomethyl]ceph-3-em-4-carboxylic acid.

* * * * *